United States Patent [19]
Liou

[11] Patent Number: 5,873,715
[45] Date of Patent: Feb. 23, 1999

[54] DENTAL DISTRACTOR

[76] Inventor: Eric Jein-Wein Liou, No.199, Tun-Hwa North Rd., Taipei, Taiwan

[21] Appl. No.: 119,213

[22] Filed: Jul. 20, 1998

[51] Int. Cl.$^6$ ..................................................... A61C 7/00
[52] U.S. Cl. .................................................. 433/18; 433/7
[58] Field of Search ................................ 433/17, 18, 23, 433/7, 12

[56] References Cited

U.S. PATENT DOCUMENTS

| | | | |
|---|---|---|---|
| 382,897 | 1/1888 | Patrick | 433/18 |
| 678,452 | 1/1901 | Schutz | 433/22 |
| 4,483,674 | 11/1984 | Schutz | 433/22 |

*Primary Examiner*—Cary E. O'Connor
*Assistant Examiner*—Patrick A. Hilsmier
*Attorney, Agent, or Firm*—W. Wayne Liauh

[57] ABSTRACT

An orthodontic dental distractor was invented for rapid orthodontic tooth movement into a fresh extraction socket. It is derived from the concept of distraction osteogenesis. The device includes a distractor head, a movable joint and a screw. The distractor head has one end engageable with a molar band mounted on a molar and another end connecting with a sliding bar on which a screw seat is fixedly mounted. The movable joint is engageable with a canine band mounted on the canine. The screw has a screw head and is engageable with the screw seat and the movable joint. By turning the screw head, the screw can drive the movable joint moving toward the screw seat and consequently moving tooth rapidly.

3 Claims, 5 Drawing Sheets

DENTAL DISTRACTOR

BACKGROUND OF THE INVENTION

1. Field of the Invention

This invention relates to a device for rapid orthodontic tooth movement into a fresh tooth extraction space for correcting severe front teeth crowding or protrusion in orthodontic treatment.

2. Description of the Prior Art

Conventional orthodontic treatment for severe anterior teeth crowding or protrusion generally takes one and half to two years. Generally, there are five steps in the treatment procedure.

1. Extracting the first premolars.
2. Initial teeth leveling by using orthodontic brackets and arch wires. Depending on the alignment of teeth, this step lasts about three to six months.
3. Retracting canine backward into the first premolar extraction space for anterior teeth. This step lasts about four to six months for children and seven to eight months for adults.
4. Retracting anterior teeth to level the protruding teeth. This step lasts about six months.
5. Fine adjustment of occlusion and tooth angulation. This step lasts about three to six months.

This treatment procedure is too long to the patients. It is not esthetic to wear braces for such a long period and it is very burdensome for the patients to maintain their oral hygiene as well. It also is very inconvenient and time-consuming for the patients to visit orthodontist's office in such a long period. Two major steps make the period of orthodontic treatment long. They are the step 3 (canine retraction) and step 4 (anterior retraction), which take a whole year in a total. Several efforts including using postaglanding injections into the periodontal ligaments have been made to shorten the time needed for these two steps. However, the results are not very convincing in the clinical point of view and it is very painful for the patients as well.

FIGS. 1 and 2 show the conventional method for canine retraction after first premolar extraction with an elastic power chain. The first molar 1 is engaged with a molar band 12 and a bracket 121 welded on the buccal surface thereof. The canine 3 is engaged with a canine band 32 and a bracket 321 welded on the buccal surface thereof. An elastic power chain 2 is engaged between the brackets 121 and 321. Through the elastic force of the elastic power chain 2, the canine 3 can be pulled gradually toward the first molar 2 and a space is left behind the canine. The regular rate of canine retraction with elastics is 1 mm per month. It takes 4–6 months to retract a canine into a desirable position accordingly. After the canine had been retracted all the way back into the first premolar space, the anterior teeth have gotten space for anterior retraction.

The strength of the elastic power chain 2 is not consistent to control the tooth movement. It absorbs saliva and deteriorates quickly in patient's mouth. It has to be changed frequently, which causes a lot of inconvenience for the patients as well. For people with a busy life and working schedule, this is simply just too long and not good enough.

SUMMARY OF THE INVENTION

The object of present invention is to provide a dental distractor that moves tooth rapidly and efficiently into a fresh extraction socket in a short period of time so that the time needed for orthodontic treatment is greatly reduced. The concept of this invention is derived from distraction osteogenesis that induces new bone formation 1 mm per day.

A preferred embodiment of a dental distractor for rapid orthodontic tooth movement after the first premolar extraction includes a first band, a second band, a distractor head, a movable joint and a screw. The first band is mounted on a molar, including two sheaths on the buccal side. The second band is mounted on a canine, including a hook soldered on the buccal side. The distractor head has an engaging end engagable with the sheaths. The sliding bar has one end connecting with the engaging end which is engaged with a screw seat where the first screw bore is formed. While the other end of the sliding bar is movable and engagable with the second screw bore. The movable joint has a connecting screw engaeable with the hook. The screw engageable with the first screw bore and the second screw bore has a screw head at one end.

Wherein turning the screw head, the screw will drive the movable joint moving toward the screw seat and subsequently moving the tooth, for example a canine, in the same direction. In this way, the tooth can be moved 6 to 7 mm in three weeks. That means the canine retraction can be completed in three weeks rather than 6 months. And subsequently, due to less resistance of the soft new bone formed by the distraction, the anterior retraction also can be done by the dental distractor in 3 to 4 months in stead of 6 months. In a total, the time needed for canine and anterior retractions is saved at least 8 to 9 months.

BRIEF DESCRIPTION OF THE DRAWINGS

The following description and draws show the invention, as well as its many advantages.

DETAILED DESCRIPTION OF THE PREFERRED EMBODIMENT

Figure 1:
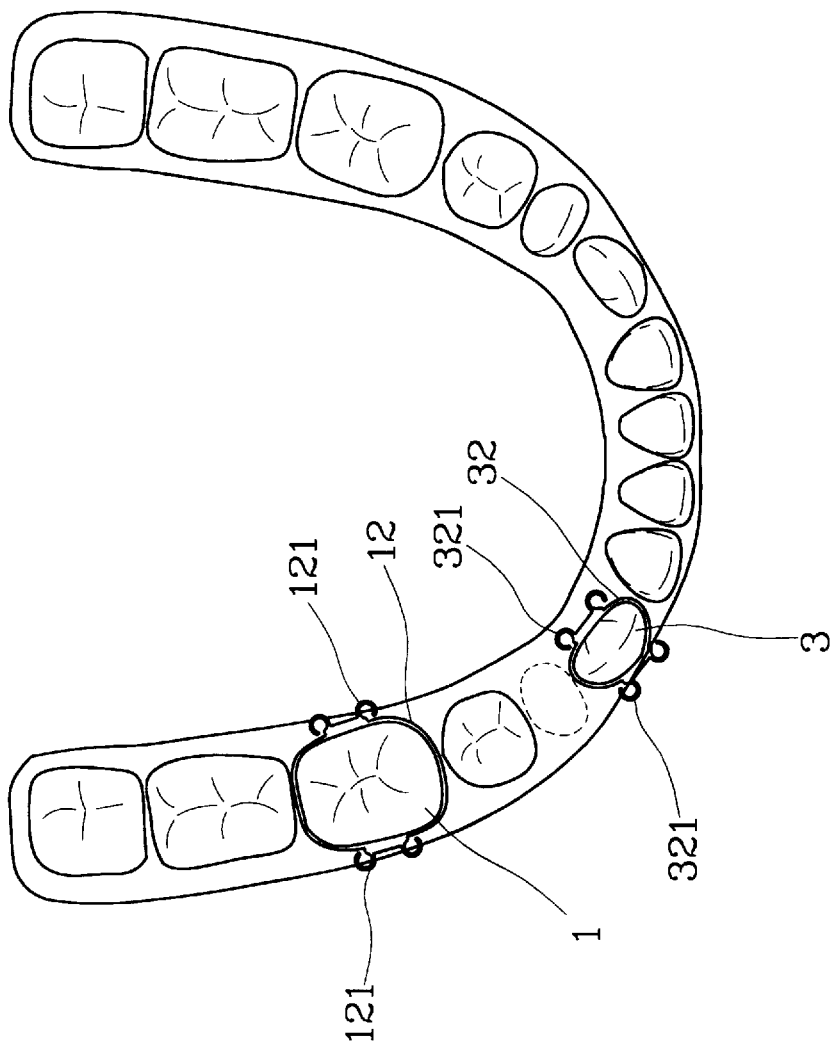
FIG. 1 is a partial top view of a conventional method in canine retraction.
Figure 2:
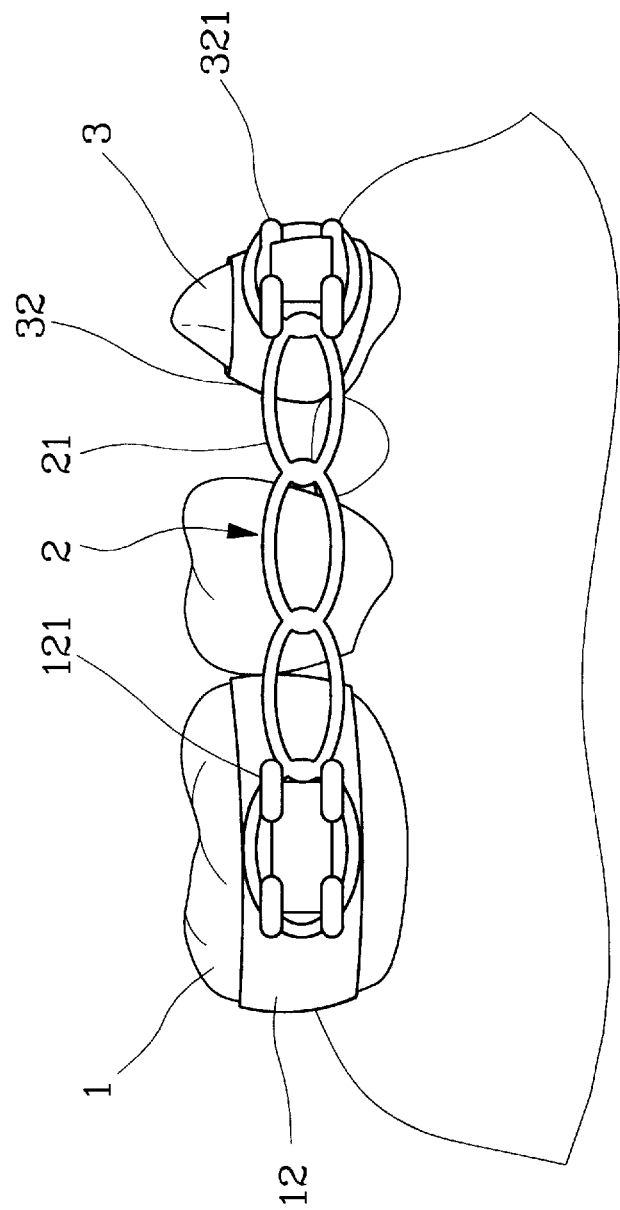
FIG. 2 is a front view of a conventional method in canine retraction.
Figure 3:
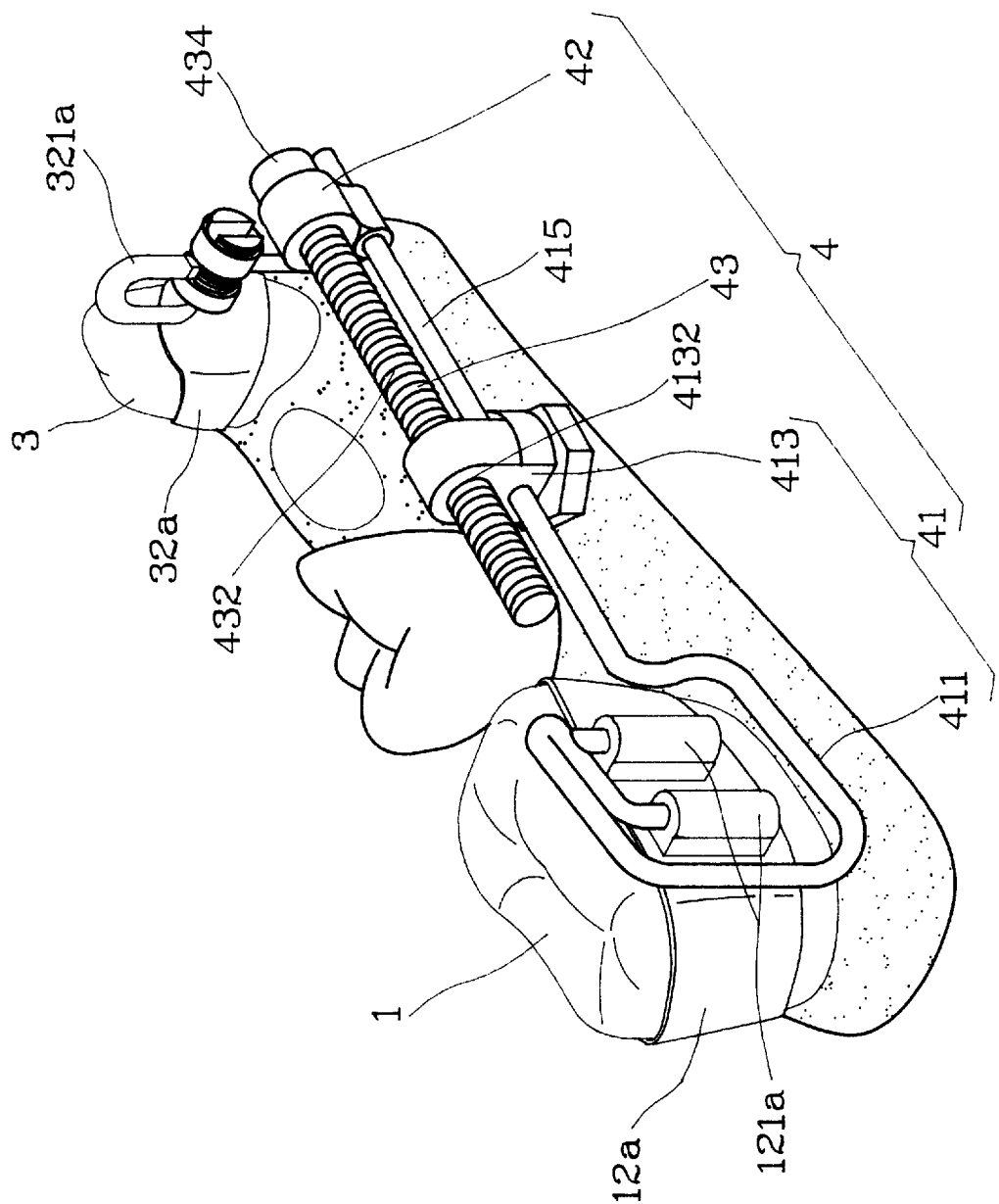
FIG. 3 is a pictorial view of this invention.

Referring to FIG. 3, the dental distractor 4 includes a distractor head 41, a movable joint 42 and a screw 43. There is a molar band 12a mounted on the first molar 1. The molar band 12a has buccal sheaths 121a welded on buccal surface. The buccal sheaths 121a have two spaced cylindrical bores located therein. The canine 3 has a canine band 32a mounted thereon. On the buccal surface of the band 32a, there is a reversed U-shaped hook 321a fixed thereon.

Figure 4:
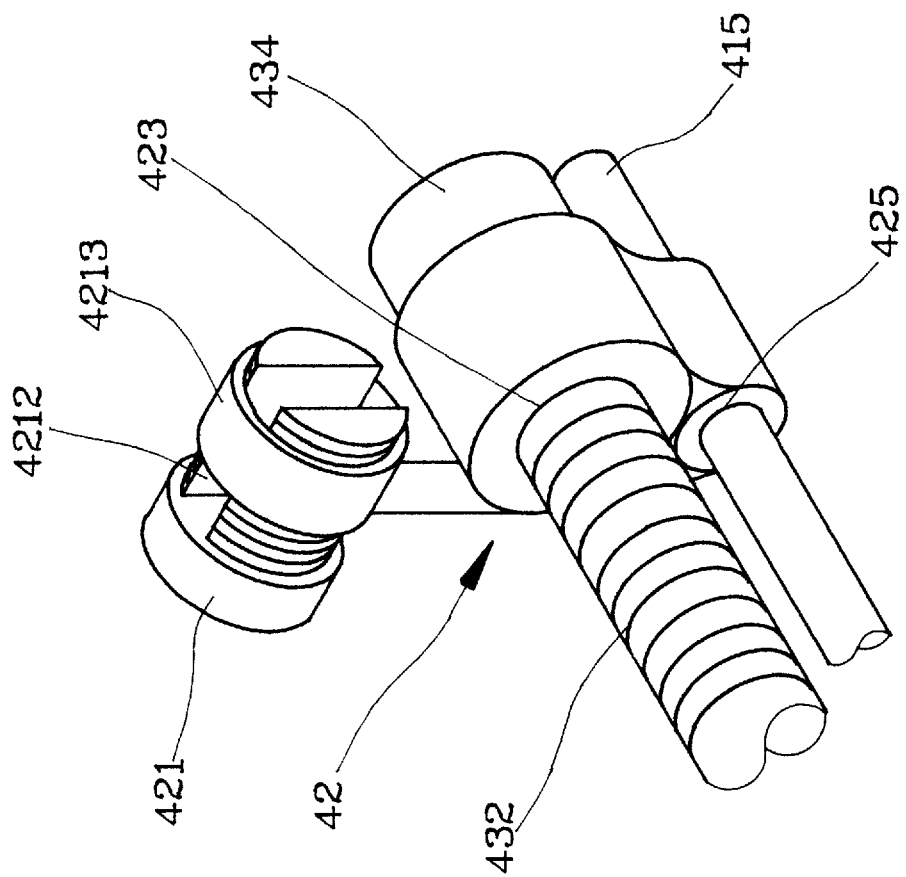
FIG. 4 is a fragmentary perspective view of this invention.

Referring to FIG. 4, the movable joint 42 includes a connecting screw 421 with a slot 4212 and a cap 4213. By driving the cap 4213 on the connecting screw 421 and then securing the hook 321a, a second screw bore 423 is engageable with a screw bar 432 of the screw 43 and a sliding bore 425. The sliding bar 415 slidably runs through the sliding bore 425. The screw 43 has a screw head 434 at one end thereof the screw bore 423.

Figure 5:
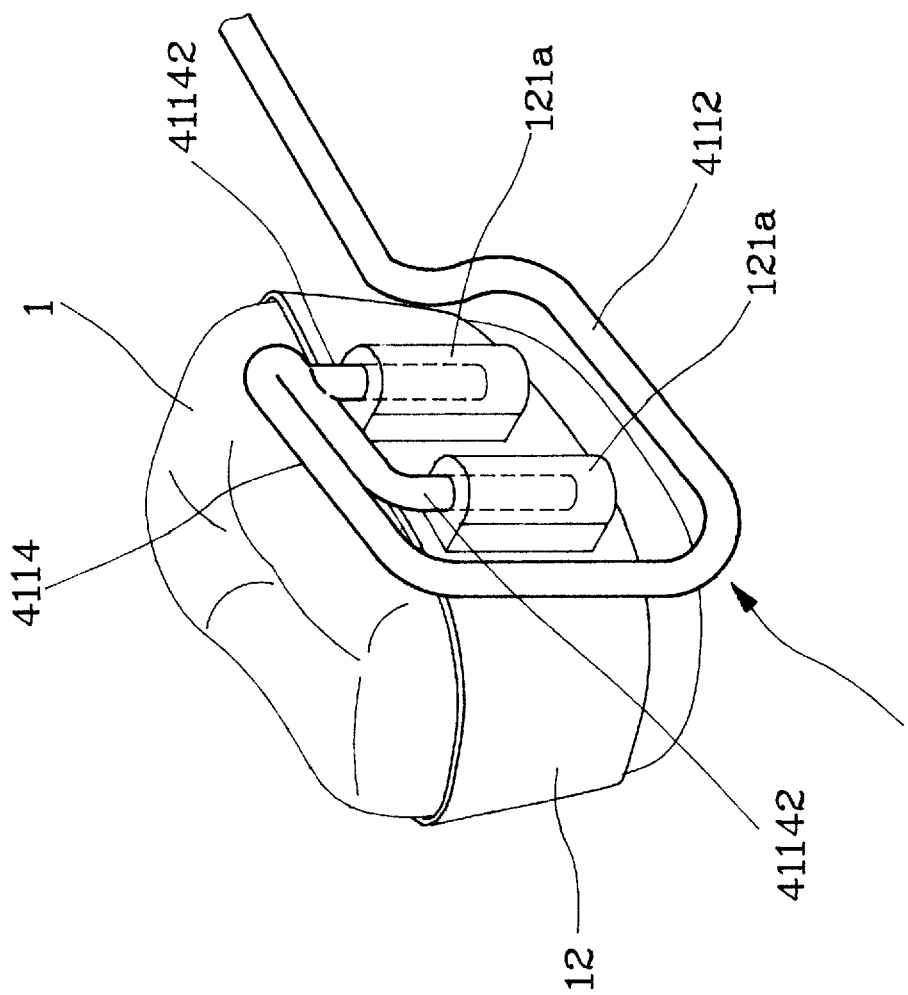
FIG. 5 is another fragmentary perspective view of this invention.

Referring to FIG. 3 and 5, the distractor head 41 includes an engaging end 411 which is substantially a ⊂-shaped bar. The engaging end 411 has an upper bar 4114 which has two legs 41142 engageable with the cylindrical bores of the buccal sheaths 121a. The engaging end 411 further has a lower bar 4112 connecting with one end of the sliding bar 415. The screw seat 413 is fixed on the sliding bar 415 and has a first screw bore 4132 engageable with the screw bar 432.

When a patient is undergoing rapid orthodontic treatment for correcting severe anterior crowding or protrusion, the canine 3 has to be moved backward with the distractor immediately after the first premolar extraction and before the new alveolar bone is generated. The molar band 12a is mounted on the first molar 1 and the canine band 32a is mounted on the canine 3 before the first premolar extraction. Immediately after the first premolar extraction, the distractor head 41 is mounted on the molar band 12a by engaging the legs 41142 into the buccal sheath 121a. The movable joint 42 is engaged with the canine band 32a by inserting the hook 321a into the slot 4212. Then the screw seat 413 is engaged with the movable joint 42 by turning the screw head 434. Each turn or a fractional turn, the screw head 434 will drive the movable joint 42 back a definite distance toward the screw seat 413. The distractor of this invention may be made of high strength alloy with stable property and bio-comparability.

By following the orthodontist's instructions, patients may turn the screw head 434 easily by using a simple tool without going to orthodontist's office. The force generating by the screw 43 and the movable joint 42 is more effective than the elastic power chain. It would not absorb saliva or deteriorate in patient's mouth. It moves tooth 6 to 7 mm in three weeks. It can greatly shorten treatment time. It is simple, convenient, effective and time-saving as well.

The following is the general procedures of using this invention to perform rapid orthodontic tooth movement:

1. Putting on orthodontic brackets for initial alignment and leveling of anterior teeth for one to two months.
2. Extracting first premolars and putting on dental distractors of this invention to move the canines within three weeks.
3. Retracting anterior teeth backward for 3 to 4 months.
4. Fine adjusting the occlusion and tooth angulation.

It may thus be seen that the objects of the present invention set forth herein, as well as those made apparent from the foregoing description, are efficiently attained. While the preferred embodiment of the invention has been set forth for purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A dental distractor for rapid orthodontic tooth movement after tooth extraction, comprising:

a band for mounting on a tooth including a buccal sheath on the buccal surface thereof;

a band for mounting on a tooth including a hook welded to the buccal surface thereof;

a distractor head having an engaging end engageable with the buccal sheath, a sliding bar having one end thereof connecting with the engaging end and a screw seat fixedly engaged with the sliding bar having a first screw bore formed therein;

a movable joint having a connecting screw engageable with the hook, a second screw bore and a sliding bore movably engaged with the sliding bar; and a screw engageable with the first screw bore and the second screw bore, said screw having a screw head at one end thereof;

wherein turning the screw head in a certain direction, the screw will drive the movable joint moving toward the screw seat and consequently moving the tooth.

2. A dental distractor of claim 1, wherein the buccal sheath includes pair of cylindrical bores, the distractor head being formed in a substantially ⊂-shaped bar with a lower bar connecting with the sliding bar and an upper bar having two legs engageable into the cylindrical bores.

3. A dental distractor of claim 1, wherein the hook is a substantially reversed U-shaped member with a free end, the connecting screw having a slot and a cap, the hook and the slot are secured by driving the cap on the connecting screw.

* * * * *